United States Patent
Austen et al.

(10) Patent No.: US 7,077,938 B1
(45) Date of Patent: Jul. 18, 2006

(54) ELECTROCHEMICAL GAS SENSOR

(75) Inventors: Malcolm Trayton Austen, Middlesex (GB); John Robert Dodgson, Surrey (GB)

(73) Assignee: Invensys Controls UK Limited, London (GB)

(*) Notice: Subject to any disclaimer, the term of this patent is extended or adjusted under 35 U.S.C. 154(b) by 315 days.

(21) Appl. No.: 10/111,201

(22) PCT Filed: Oct. 26, 2000

(86) PCT No.: PCT/GB00/04132

§ 371 (c)(1),
(2), (4) Date: Aug. 30, 2002

(87) PCT Pub. No.: WO01/31327

PCT Pub. Date: May 3, 2001

(30) Foreign Application Priority Data

Oct. 26, 1999 (GB) .................................. 9925187.8

(51) Int. Cl.
*G01N 27/404* (2006.01)

(52) U.S. Cl. ...................................... 204/431; 204/432
(58) Field of Classification Search ........ 204/424–429, 204/431, 432
See application file for complete search history.

(56) References Cited

U.S. PATENT DOCUMENTS

| 5,173,166 A | 12/1992 | Tomantschger et al. |
| 5,183,550 A | 2/1993 | Mattiessen |
| 5,914,019 A | 6/1999 | Dodgson et al. |

FOREIGN PATENT DOCUMENTS

| EP | 0 762 116 A1 | 3/1997 |
| EP | 0 902 281 A2 | 3/1999 |
| WO | WO 9825138 A1 * | 6/1998 |
| WO | WO 99/24826 A1 | 5/1999 |

* cited by examiner

*Primary Examiner*—Kaj K. Olsen
(74) *Attorney, Agent, or Firm*—Andrus, Sceales, Starke & Sawall, LLP

(57) ABSTRACT

The present invention relates to an electrochemical gas sensor that includes a first planar substrate having at least one planar electrode formed thereon, thereby forming a first electrode assembly, and a housing defining a reservoir which, in use, contains liquid electrolyte for contacting the electrode(s). The housing has a first sealing face to which the first electrode assembly is sealed, the sealing face having conducting portions electrically isolated one from another. A portion of at least one electrode is in contact with a respective conducting portion so as to provide a means of external electrical connection to the electrode(s). The conductive portions and non-conductive portions of the housing are co-moulded. This sensor has a relatively small number of component parts and is relatively cheap and easy to manufacture. It also provides a cheap and reliable way of forming external electrical connections to the electrodes.

5 Claims, 4 Drawing Sheets

ELECTROCHEMICAL GAS SENSOR

TECHNICAL FIELD

The present invention relates to an electrochemical gas sensor. It relates particularly, but not exclusively, to an electrochemical gas sensor for sensing carbon monoxide gas.

BACKGROUND ART

An electrochemical gas sensor for sensing an oxidisible or reducible gas (e.g. carbon monoxide) in the atmosphere usually contains a sensing or working electrode, a counter electrode and an inlet (usually a diffusion barrier) to allow the atmosphere to permeate to the sensing electrode. Both electrodes are in contact with an electrolyte in order to produce an electrochemical reaction at the sensing electrode with the gas to be sensed, and to produce an electrochemical reaction at the counter electrode with oxygen in the atmosphere, electrolyte or other gas source. Electric current is carried through the electrolyte by ions produced in the reaction and by electrons through an external circuit, the current in the circuit indicating the gas concentration.

Electrochemical sensors containing liquid electrolyte require electrical contact to be made between the electrodes in contact with the electrolyte and the outside world, while at the same time sealing the sensor to prevent the leakage of electrolyte. This is most often achieved by the use of metallic leads which protrude through the seal. This technique suffers from several drawbacks. Firstly, the seal around the metal leads must be made carefully to avoid leakage of the electrolyte over the long life of the cell. In addition, the strength of the contact between the metal wire and the electrodes often depends on the extent to which the parts of the sensor are compressed. The compression of these parts may be lessened if the components relax, or if the gas sensor is subjected to external forces. The assembly of a gas sensor having metallic contacts may be awkward and therefore expensive. Moreover, the electrolyte is often corrosive and so noble metal contacts such as platinum must be used. This increases the cost of manufacture of the gas sensor.

The aforementioned problems also occur where solid polymer electrolyte is used, because a hygroscopic electrolyte is usually included in the cell housing in order to keep the polymer hydrated. These problems have largely been solved, as described in U.S. Pat. No. 5,914,019 (Dodgson et al) by using conductive polymer to seal the electrodes and the contacts. Gas sensors manufactured in this way have proved reliable and easy to fabricate. However, the move towards ever smaller sensors has meant that redesign of the electrical contacts to save space is advantageous.

U.S. Pat. No. 5,173,166 (Tomantschger et al) describes a sensor in which electrodes are mounted in conductive polymer frame members separated by an insulating frame member, the members being bonded together to form a leak-tight housing. This arrangement removes the need for contact pins. However, frame members are very large and so distances between electrodes and external contacts are relatively large. This means that polymer must contain high levels of carbon so that its conductivity is maintained, but the inclusion of high levels of carbon makes the polymer difficult to process and to use. The resulting gas sensor cell is then structurally weak and slow to assemble—it takes typically ten minutes to bond the assembly at a temperature of 165° C. The carbon loaded polymer does not allow fine features to be moulded from it. For example, the filling hole (where electrolyte is introduced into the sensor) must be drilled after the gas sensor has been assembled.

A similar design of gas sensor to that described in U.S. Pat. No. 5,173,166, is disclosed in European Patent Application No. EP-A2-0902281 (Senco). Here, the gas sensor housing includes of a stack of conductive polymer frame members which are separated by non-conductive frame members. Electrodes are bonded to the conductive polymer members using heat. The gas sensor suffers from the same sort of problems as the gas sensor described in U.S. Pat. No. 5,173,166 (Tomantschger) in that all of the joints between individual frame member must be leak-tight. The gas sensor also has a relatively large number of components, and assembly of the sensor is therefore a slow and costly process. In general, the use of conductive polymer for frame-like components of a gas sensor appears to be disadvantageous.

An aim of the present invention is to provide a gas sensor which has a relatively small number of component parts and is therefore relatively cheap and easy to manufacture. Another aim of the invention is to provide a cheap and reliable way of forming external electrical connections to a gas sensor. A further aim of the invention is to produce a more compact sensor.

SUMMARY OF INVENTION

According to the invention there is provided an electrochemical gas sensor that includes a first planar substrate having at least one planar electrode formed thereon, thereby forming a first electrode assembly, and a housing defining a reservoir which, in use, contains liquid electrolyte for contacting the electrode(s). The housing has a first sealing face to which the first electrode assembly is sealed, the sealing face having conducting portions electrically isolated one from another. A portion of at least one electrode is in contact with a respective conducting portion so as to provide a means of external electrical connection to the electrode(s). The conductive portions and non-conductive portions of the housing are co-moulded. This sensor has a relatively small number of component parts and is relatively cheap and easy to manufacture. It also provides a cheap and reliable way of forming external electrical connections to the electrodes.

BRIEF DESCRIPTION OF DRAWINGS

Embodiments of the invention will now be described, by way of example only, with reference to the accompanying Figures, in which:—

FIG. 1b shows a plan view of the gas sensor shown in FIG. 1a;

FIG. 2b shows a plan view of the gas sensor of FIG. 2a;

FIGS. 2c and 2d show a portion of the gas sensor of FIG. 2a;

DETAILED DESCRIPTION OF PREFERRED EMBODIMENTS

Figure 1A:
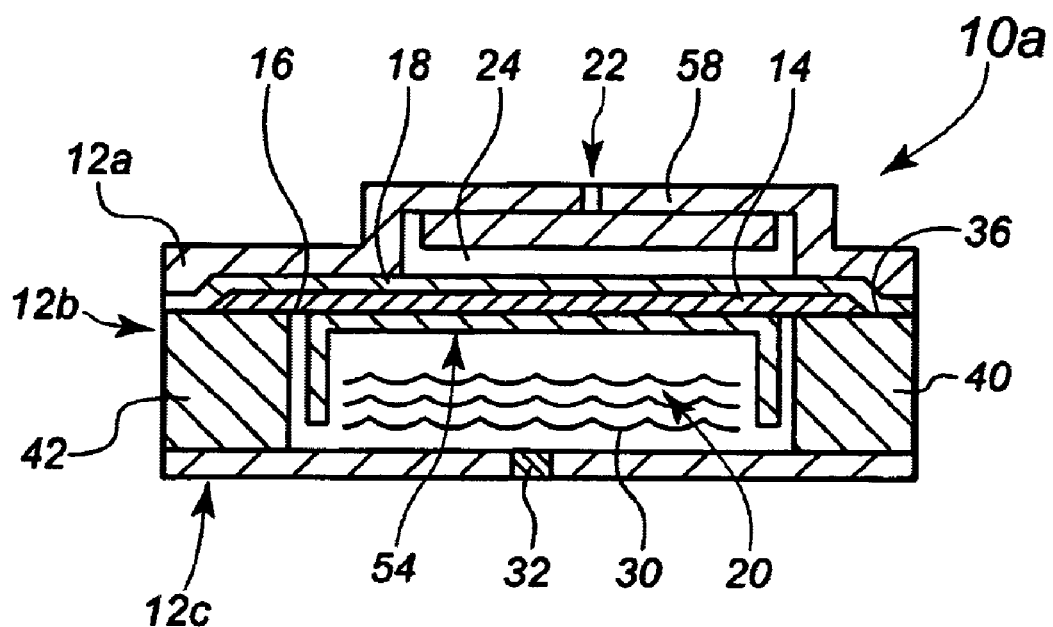
FIG. 1a shows a cross-section of a first gas sensor.

Referring to FIG. 1a, there is shown a generally cylindrical electrochemical gas sensor (10a) comprising a three-part housing (12), namely a body part (12b) which is cylindrical with a hollow interior for forming an electrolyte reservoir (20), a disc-shaped cap member (12a), and a disc-shaped lid (12c). A porous flexible membrane (18) in the form of a disc is disposed between body member (12b) and cap member (12a). The housing (12) can have a groove defined therein, the groove being dimensioned so as to retain the flexible membrane substrate (18).

Sensing (14), reference (15) (not shown), counter (16) electrodes, and optional test gas generation electrodes (not shown), all formed from a mixture of electrically conductive catalyst particles in PTFE (or similar polymeric) binder, are formed on the lower surface of the substrate (18) to form an electrode assembly. The electrodes can be screen printed, filter deposited, or sintered (or any other method suitable for producing segments of the mixture) onto the substrate (18). As an alternative to the mixture of the catalyst particles and PTFE binder, a single material can be deposited onto the substrate (18), followed by the subsequent deposit of other materials. This may be used to vary the properties of the electrode material through its thickness, or to add a second layer of increased electrical conductivity above or below the layer which is the main site of gas reaction.

The cap member (12a) has through-hole (22) formed therein leading to a recessed manifold area (24) for permitting atmospheric gas to diffuse through aperture (22) and thence, via manifold area (24), through substrate (18) to the sensing electrode (14). The cap member (12a) is shaped so that access of atmospheric gas to the reference electrode (15) (and optionally the counter electrode (16)) is blocked. A filter (58) is provided to remove unwanted gas and/or particulates. The cap member (12a) may also include a diffusion barrier (not shown) to limit the amount of gas reaching the sensing electrode (14).

Electrolyte (30) within electrolyte reservoir (20) is maintained in contact with the electrodes by means of a wick (54). The reservoir (20) is closed at the base by lid (12c) having a base member (32) comprising a pressure relief aperture closed by a porous membrane.

A surface of the housing (12b) to which the electrode membrane (18) and the electrodes formed thereon is attached is hereinafter referred to as a 'sealing face'.

Figure 1B:
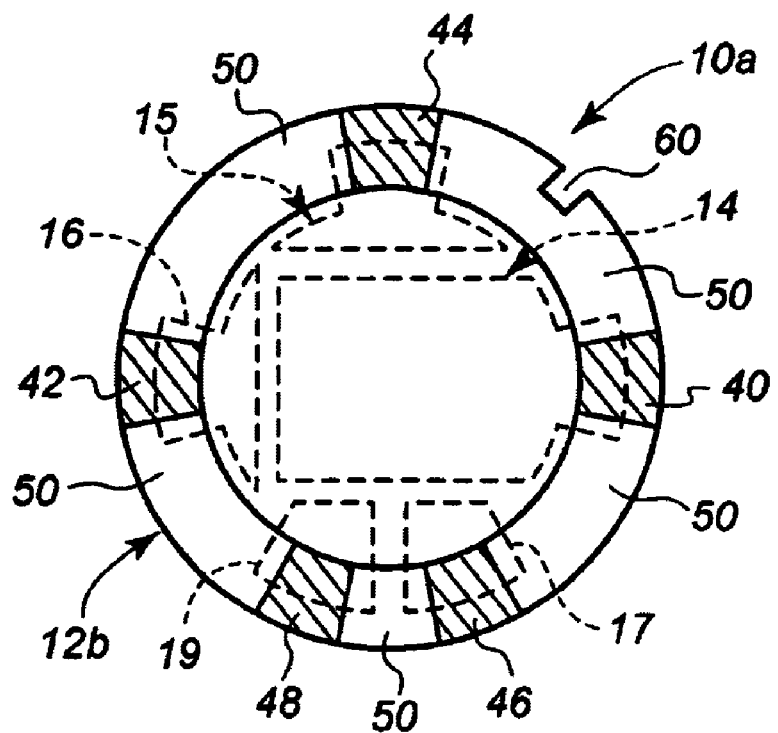

Referring now to FIG. 1b, housing body part (12b) comprises alternating non-conducting polymer (50) and conducting polymer (40,42,44,46,48) portions. Each portion of conducting polymer (40,42,44,46,48) is positioned adjacent an electrode (14,16,15,17,19) and sealed thereto via sealing face (36) so as to form areas of conduction on the housing which may be used for external electrical connection to the sensor (10a).

As shown in FIG. 1b, a portion of the electrode may also be sealed to a non-conducting part of the housing (50) which lies adjacent a conducting portion. This construction has the advantage that, in the case of a better seal being made to the non-conducting than the conducting region, there is less chance of leakage of electrolyte via the seal between the electrode and the housing.

The conducting polymer portions (40,42,44,46,48) extend from the inner surface of the housing body part (12b) to the outer surface of the housing body part. The conductive and non-conductive regions of the housing can be made of the same polymer, with the conductive regions being loaded with conductive particles. A positioning notch (60) is formed in body part (12b) and also in membrane (18) so that alignment of the electrodes (14,16,15,17,19) and the conducting portions (40,42,44,46,48) is achieved. A conducting region of the housing may also function as an electrode, particularly a counter electrode. This saves enables the area of the sensing electrode to be increased, or allows a smaller sensor to be made.

Figure 2A:
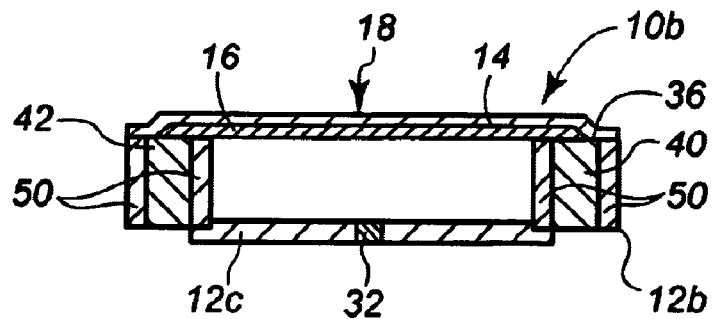
FIG. 2a shows a cross-section of a second gas sensor.
Figure 2B:
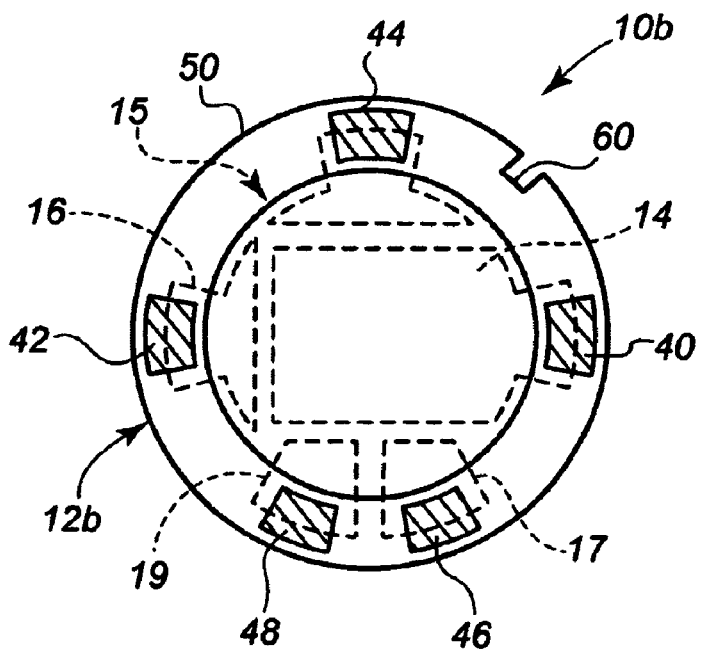

Referring now to FIGS. 2a and 2b, there is shown a second gas sensor cell (10b) similar to that shown in FIGS. 1a and 1b, but wherein the sides of the conducting polymer portions (40,42,44,46,48) are surrounded by non-conducting housing material. In this case, external electrical connection is made to the areas of the conducting polymer portions (40,42,44,46,48), which are accessible at the base of the sensor (10b).

Figure 2C:
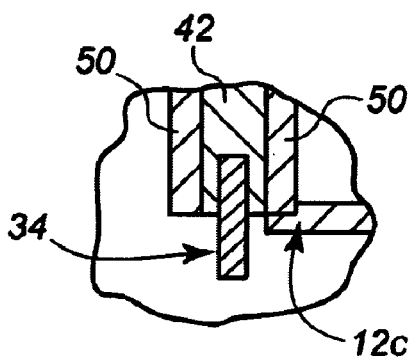
Figure 2D:
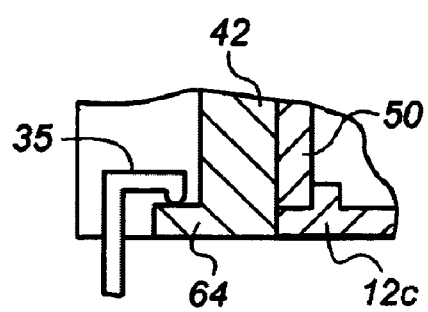

In FIG. 2c there is shown a section of sensor (10b) wherein external electrical connections are made by means of contact pins (34) which are inserted into each conducting polymer portion (40,42,44,46,48) via the base of the sensor. In FIG. 2d, there is shown a conducting polymer portion (42) of body part (12b) which has a lip (64) at its base and a barbed contact pin (35). The barbed contact pin (35) fits over the lip (64) to give a form of bayonet retention in which a push and twist action locks the sensor cell in place.

Figure 3A:
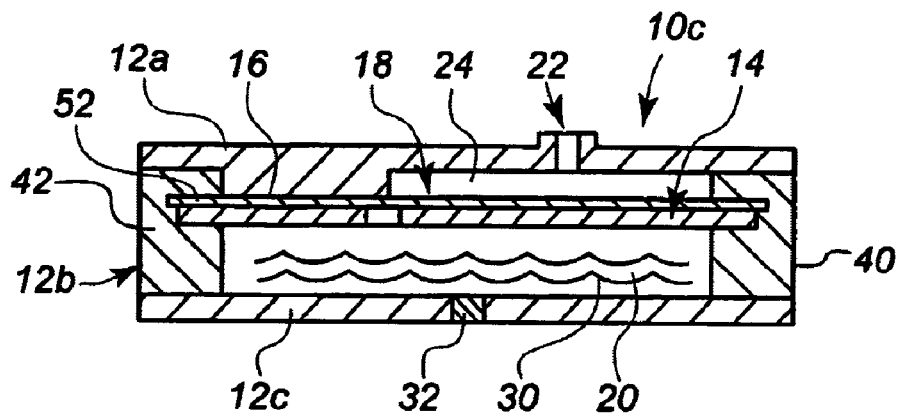
FIG. 3a shows a cross-section of a further gas sensor.

FIG. 3a shows another gas sensor (10c) which also comprises a generally circular three-part housing (12a,b,c) having conductive and non-conductive regions, a disc-shaped membrane (18) having electrodes formed thereon, an electrolyte reservoir (20) containing liquid electrolyte (30) and a wick (not shown). In this case, the body part (12b) is moulded around the membrane (18) which gives a good seal and conductive contact in an integral assembly. A sensor which includes a stacked electrode assembly (as disclosed in the Applicant's co-pending International Patent Application No. PCT/GB98/03363) may also be moulded into body part (12b). This method of constructing a gas sensor may be achieved by insert moulding the electrode membrane (18) into the housing (12b).

As in the aforedescribed sensors, external electrical connection to the sensor (10c) is made via the conducting polymer portions (40,42) which may extend from the inner to the outer surface of body part (12b), or the conducting portions may be partially surrounded by non-conducting polymer (50) so that the conducting portions are accessible only at certain areas of the body part (12b).

Figure 3B:
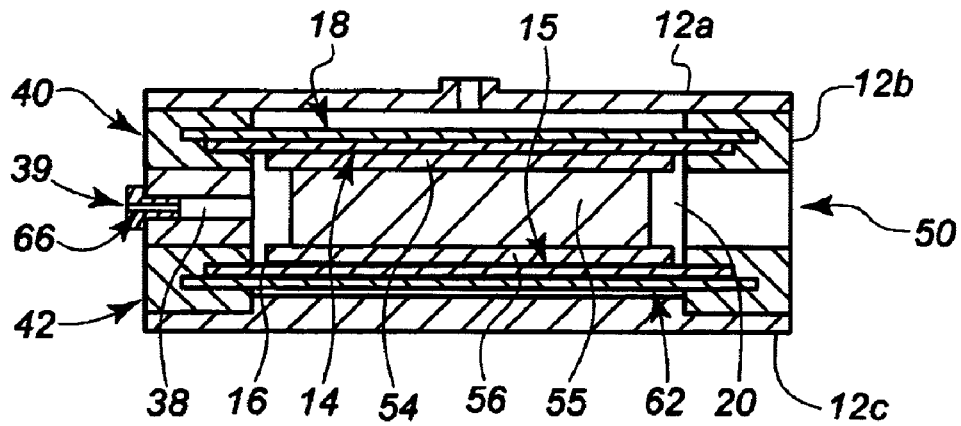
FIG. 3b shows a cross-section of another gas sensor.

A similar gas sensor to that shown in FIG. 3a is shown in FIG. 3b. This gas sensor can also be formed by insert moulding of the electrode assembly (i.e., electrode (14) formed on electrode membrane (18)) into the housing (12b). Insert moulding is carried out by placing the electrode assembly into an appropriate position within a mould, then flowing molten polymer around the assembly to form the housing. Simultaneously, or in a subsequent step in the same moulding process, further material can be added to create partitions over the area of the assembly, or to build up material of a second type onto, or around, the first material.

In the sensor shown in FIG. 3b, a first electrode assembly (14,18) is moulded into a portion of conducting polymer (40). A second electrode assembly (15,16,62), disposed parallel to the first electrode assembly, is similarly insert moulded into another portion of conducting polymer (42). The manufacture of the housing (12) is completed by sealing the two housing parts to a further portion of non-conducting material (50).

The electrodes formed on the first (18) and second (62) electrode membranes are in contact with wicks (54) and (56), respectively. The wicks (54,56) are held in place by a volume of compressible absorbent material (55). The electrolyte reservoir (20) is filled with electrolyte through a channel (38) which extends through the side of the housing, and is sealed by a filler plug (39). A breather means (66) for the use of pressure relief is formed within the filler plug (39). Alternatively, the breather means can be located elsewhere in the housing (12).

As in aforedescribed sensors, a cap member (12*a*) is provided to allow, and control, gas access to the first electrode assembly (14, 18). A lid (12*c*) is also provided in order to prevent gas from reaching the reference (15) and counter electrodes which are formed on the second electrode membrane (62).

The advantage of the sensors shown in FIG. 3 is that, by moulding the electrode assembly (or assemblies) together with the housing, the number of manufacturing steps is reduced. In addition, this method of manufacturing the sensor leads to a more robust sensor which is less prone to leakage as only one fluid-tight seal is required.

Figure 4:
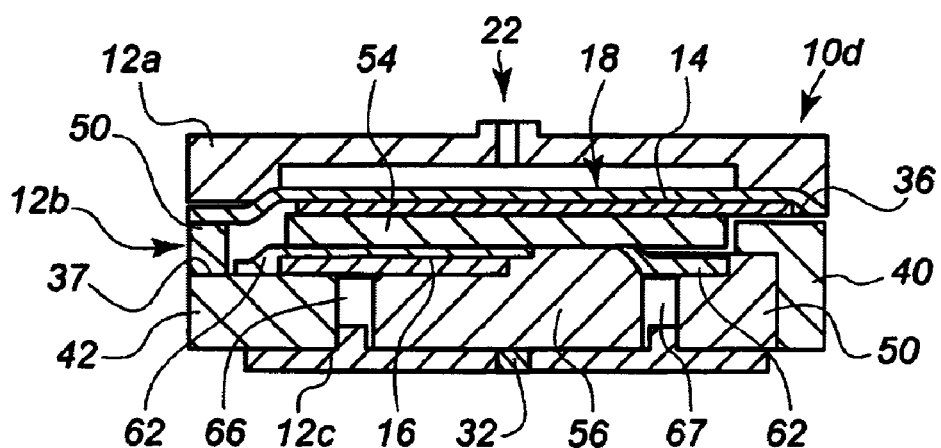
FIG. 4 shows a cross-section of a further gas sensor.

A further gas sensor (10*d*) is shown in FIG. 4. This sensor has a stacked electrode arrangement, and a generally circular three-part housing which includes a hollow body part (12*b*) composed of conducting and non-conducting portions. A first disc-shaped membrane (18) has a sensing electrode (14) formed on the lower surface thereof, and is of the same (or smaller) diameter as the cap member (12*a*) and body part (12*b*). Electrode (14) is in contact with a wick (54), which in turn is in contact on its lower surface with the upper surface of a disc-shaped second membrane (62). A counter electrode (16) and/or reference electrode is formed on the lower surface of the second membrane (62), and is in contact with a second wick (56). Second membrane (62) has an aperture formed therein so that the second wick (56) contacts a portion of the first wick (54). In this sensor, compression of the wicks (54) and (56) is used to maintain contact between them. An electrolyte reservoir (67) is provided by leaving a space between wick (56) and the inner wall of body part (12*b*). Housing 12 includes a second sealing face 37 to which the counter electrode 16 and membrane 12 sealed.

Figure 5:
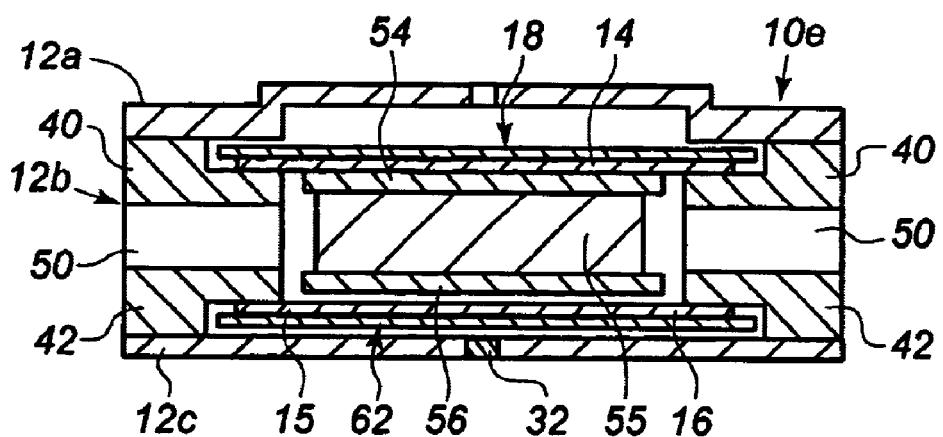
FIG. 5 shows a cross-sectional view of a further gas sensor.

FIG. 5 shows a sectional view of a further sensor (10*e*). This sensor uses a stacked electrode arrangement, where the components common to the previous embodiments have the same reference numbers. The housing body part (12*b*) is formed of conductive portions (40,42) and a non-conductive portion (50) in a stacked assembly—the non-conductive portion (50) being disposed between the conductive portions (40,42). Electrode (14) is mounted on a first electrode membrane (18) and sealed to the upper conductive portion (40) of the housing (12*b*), forming an electrical connection thereto. Electrodes (15) and (16) are mounted on a second electrode membrane (62), and outer parts of these electrodes are sealed to the lower conductive portion (42) of the housing body part (12*b*). In plan view, the sensor (10*e*) looks similar to the sensor (10*a*) shown in FIG. 1*b*, except that the electrodes of sensor (10*e*) are not all in the same plane.

A first wick (54) is placed in contact with sensing electrode (14), and a second wick (56) is in contact with the electrodes (15,16) on the second electrode membrane (62). Wicks (54) and (56) are maintained in position by a wick retaining means (55) which may be, for example, a lightly compressed volume of plastic foam.

An electrolyte fill channel (not shown) extending through the housing body part (12*b*) into the electrolyte reservoir (20) may be provided, the channel being closed by a plug including a breather means (also not shown).

The housing can be assembled by sealing the cap member (12*a*), the three separate conductive (40,42) and non-conductive portions (50) of housing body part (12*b*), and the lid (12*c*) together using heat and pressure, or by using a method such as ultrasonic bonding. However, the electrode membrane (18) and the electrode (14) formed thereon can be incorporated into the body part at the time of moulding, i.e., the body part can be moulded around the electrode assembly (14,18) using injection moulding.

Figure 6:
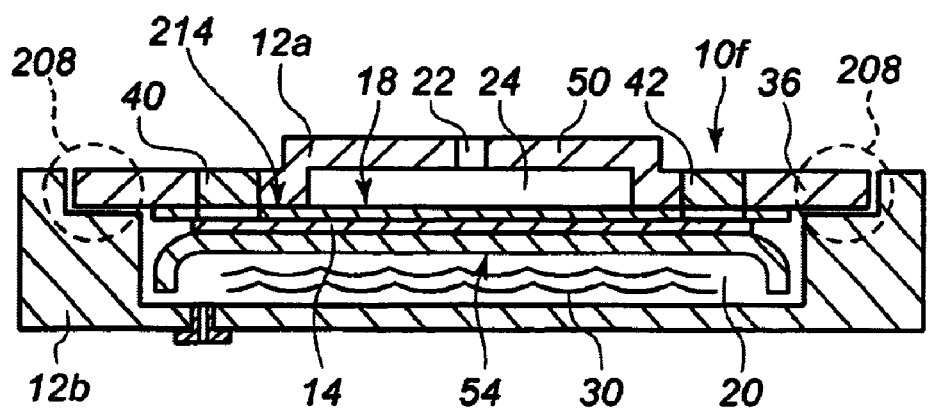
FIG. 6 shows a cross-sectional view of another gas sensor.

A further gas sensor (10*f*) is shown in FIG. 6. This gas sensor has a two part housing: a body part (12*b*) which defines an electrolyte reservoir (20), and a cap member (12*a*). In this case, the cap member (12*a*) has two conducting regions (40, 42) which are separated by non-conducting regions (50). The cap member (12*a*) is co-moulded so that it is an integral unit formed of conductive and non-conductive material. As described previously, electrodes are formed on an electrode membrane (18).

The cap member (12*a*) has a sealing face (36) to which to the electrode membrane (18) is sealed using, for example, heat and pressure, or ultra-sonic sealing. The cap member (12*a*) is sealed to the housing body part (12*b*) using, for example, heat, ultrasound, adhesive, or a snap-fit, so that a "fluid-tight" seal is formed in the regions (208) shown in the figure. The design of the conducting polymer regions (40, 42) is such that during the process of sealing the electrode membrane (18) to the housing, the conducting polymer material is urged through the membrane and into the electrode(s) formed thereon. Electrical contact to the conducting polymer regions (40, 42) can be made either by press contact to their upper faces, or by the use of, for example, contact pins inserted into the conducting polymer (not shown). Wick 54 is attached to the bottom of electrode 14.

During operation of the sensors (10), atmospheric gas ingresses through aperture (22) into manifold area (24). The aperture (22) functions as a diffusion barrier and controls the rate of gas inflow. The gas flows through the substrate (18) and into contact with sensing electrode (14). When the gas to be sensed is present in the atmosphere, it reacts at the sensing electrode (14) which produces ions in the electrolyte (30). At the counter electrode (16), oxygen in the electrolyte (30) reacts with the ions released by the sensing electrode to complete an electrical circuit, the resulting current indicating the concentration of the gas present.

Referring to all of the embodiments of the invention, external contact to the conductive portions of the housing (12) may be by pins 1) mounted on the external surface of the housing, or 2) projecting into the relevant conductive portions of the housing external contacts which press against the conductive polymer, or by shaping the conductive portions so that they themselves act as the contact means.

An advantage of the present invention is that the conducting polymer regions and the non-conducting polymer regions of the housing are co-moulded, i.e., two polymers can be moulded in the same mould. Co-moulding gives a housing which is less prone to leakage. It also enables a more complex structure of non-conducting and conducting regions of the housing to be produced, as it is more difficult to manufacture many separate parts which are subsequently joined together. The more complex housing structure also enables a more compact sensor to be produced, as more than one electrode can be formed on a single electrode membrane and it is still possible to seal each electrode to a conductive region of the housing. In the Senco patent application referred to herein, the more electrodes this sensor has, the more conducting layers are required, and the larger the sensor will be.

Two practical methods of co-moulding that can be used to produce the sensors disclosed herein are: 1) core back, and 2) rotation exchange. In the core back method, the bulk of the housing is produced by injecting molten plastic/polymer into a cavity defined by a mould tool having two or more parts. Part of the mould tool (the core) is then moved back to leave a further cavity which is defined partly by the mould tool, and partly by the first plastic moulding. The second material (in this case the conductive polymer) is then injected into the new cavity. By careful selection of the materials used, the timing and shape of the moulding, the parts of the housing may be permanently joined to produce a single component.

In the rotation exchange method, the bulk of the housing body is moulded using a first mould tool. The tool is then split, and the part containing the moulding is rotated to align with a further mould tool so as to define a new space which is the shape of the second component. The second material is then injected into this space to form a second moulding within and joined to the first. As with the core back method, careful selection of the materials, timing and shape of the mouldings allows the mouldings to be permanently joined to produce a single component.

In these methods, the materials used for the main and the second moulding need to have properties which enable them to be moulded in the same moulding machine, and to form a single joined component. A suitable combination of materials is, for example, 20% talc-filled polypropylene for the main moulding, and polypropylene compounded with carbon for the second moulding. If the two materials are produced from the same grade polypropylene then this aids the co-moulding process. Suitable carbon loading ratios for the second material are in the range 10% to 40%. Higher carbon content gives higher conductivity but the material is more difficult to mould, whereas a lower carbon content gives a material with lower conductivity but which is more easily moulded.

A further method of co-moulding a gas sensor as described herein is to 1) mould the non-conductive portion of the housing, 2) seal an electrode assembly to this portion of the housing, and 3) mould the remaining, conductive portions of the housing, or vice versa.

A further advantage of the present invention is that two or more electrodes may be shorted together so that, when the gas sensor is to be installed after transportation, the electrodes are close to electrochemical equilibrium. Shorting of the electrodes may be achieved by simply using a conductive member, such as for example, an adhesive label contacting the conducting regions. The label may then be removed before the sensor is installed. It is known that it is more difficult to short the electrodes if contact pins are present.

Variation may be made to the aforementioned embodiments without departing from the scope of the invention. For example, the lid may be incorporated into body part (12b) so that only a two-part housing is required. Alternatively, the lid may be replaced with a membrane having electrodes formed thereon, the electrodes being bonded to the conductive portions of the housing. A reference electrode may be employed in combination with a potentiostat circuit in order to maintain the potential difference between the sensing electrode and the cell electrolyte. This increases the stability of operation of the gas sensor. The gas sensor may also include a test gas generation cell in order to provide a gas sensor with a self-test facility.

The invention claimed is:

1. An electrochemical gas sensor, comprising:
    an electrode assembly including a first planar substrate having a first surface and a second surface, the second surface having at least one planar electrode formed thereon;
    a housing having a cap member and a body, the body defining a reservoir which, in use, holds liquid electrolyte for contact with the at least one planar electrode, the body being molded around the electrode assembly such that the body is in contact with both the first and second surfaces of the first planar substrate, the body having electrically conductive polymer portions and nonconductive portions being co-moulded with each other, wherein each of the electrically conductive polymer portions is accessible from an exterior of the housing, wherein each of the electrically conductive polymer portions is isolated from the other electrically conductive polymer portions by the nonconductive portions,
    wherein the cap member is sealed to a portion of the body facing the first surface of the first planar substrate;
    wherein a portion of the at least one planar electrode is sealed to the electrically conductive polymer portions of the housing and where each of the electrically conductive polymer portions extends from an interior of the housing that defines the reservoir to the exterior of the housing.

2. An electrochemical gas sensor according to claim 1 wherein at least one of said conductive portions functions as an electrode.

3. An electrochemical gas sensor according to claim 1 further including a second planar substrate disposed substantially parallel to the first substrate, said second substrate having at least one electrode formed thereon, thereby forming a second electrode assembly, the second planar substrate having a first surface and a second surface, the body of the housing being molded around the second electrode assembly such that the body is in contact with both the first and second surfaces of the second planar substrate.

4. The electrochemical gas sensor of claim 3 wherein the electrically conductive polymer portions and non-conductive portions of the body are molded around the second electrode assembly.

5. The electrochemical gas sensor of claim 1 wherein the electrically conductive polymer portions and non-conductive portions of the body are molded around the electrode assembly.

* * * * *